US005693835A

United States Patent [19]

Konishi et al.

[11] Patent Number: 5,693,835

[45] Date of Patent: Dec. 2, 1997

[54] FISH OIL HAVING DECREASED FISH ODOR AND A METHOD FOR PREPARING THE SAME

[75] Inventors: Hiroaki Konishi, Kawagoe; Kiyoshi Tatsumi, Iruma; Norifumi Sato, Kawagoe, all of Japan

[73] Assignee: Snow Brand Milk Products Co., Ltd., Hokkaido, Japan

[21] Appl. No.: 378,276

[22] Filed: Jan. 26, 1995

[30] Foreign Application Priority Data

| | | | |
|---|---|---|---|
| Jan. 27, 1994 | [JP] | Japan | 6-024750 |
| Mar. 31, 1994 | [JP] | Japan | 6-087430 |
| Mar. 31, 1994 | [JP] | Japan | 6-087433 |
| Mar. 31, 1994 | [JP] | Japan | 6-088091 |

[51] Int. Cl.$^6$ .......... C07C 51/36

[52] U.S. Cl. .......... 554/141; 554/144; 554/145

[58] Field of Search .......... 554/141, 144, 554/145

[56] References Cited

PUBLICATIONS

JAOCS, vol. 66, No. 7, Jul., 1989; "Evaluation of Compounds Contributing Characterized Fishy Flavors in Fish Oils"; C. Karahadian, et al.

AOCS Official Method; Cd. 14-16; pp. 1-6; Sampling and Analysis of Commercial Fats and Oils; "Isolated Trans Isomers—Infrared Spectrophotometric Method". 1984.

CMC 'Shokuhin to Kaihatsu'; Mar. 1992; "Development and Applications of Functional Lipid"; K. Sato, et al.; pp. 142-168.

Foods and Developments Thereof, vol. 27, No. 8, pp. 6-9; "Physiological Functions of n-3 Fatty Acids"; H. Suzuki, 1990.

Oil and Fat Chemistry Handbook, 3rd Addition, Feb. 28, 1990, p. 111; "Oil and Fat Chemistry Handbook"; Japan Oil Chemistry Institution.

Foods, Productions, Imports and Consumption, 1993, Sep. 20, 1993, pp. 3-7, 10-13 & 18-21; "Foods, Productions, Imports and Consumption"; Food Marketing Research.

Chemical Abstracts, vol. 109, 1988, 212 774.

Chemical Abstracts, vol. 111, 1989, 152455.

*Primary Examiner*—Gary Geist
*Assistant Examiner*—Deborah D. Carr
*Attorney, Agent, or Firm*—Townsend & Banta

[57] ABSTRACT

A method for preparing fish oil having decreased fish odor, which comprises slightly hydrogenating fish oil to have decrease rate of iodine value of 15% or less and decrease rate of highly unsaturated fatty acid of 33% or less. A method for preparing fish oil having decreased fish odor, which comprises slightly hydrogenating fish oil under the following non-selective conditions: (1) an amount of catalyst used in the hydrogenation is 0.05% by weight or more to an amount of the fish oil; (2) hydrogen pressure in gaseous phase at the beginning of the hydrogenation is 3 kg/cm$^2$ or more; (3) reaction temperature of the hydrogenation is in the range from 90° to 150° C.; (4) reaction time of the hydrogenation is in the range from 5 to 30 minutes. The fish oil is preferably sardine oil, mackerel oil, skipjack oil, tuna oil, skipjack orbital fat or tuna orbital fat.

17 Claims, No Drawings

FISH OIL HAVING DECREASED FISH ODOR AND A METHOD FOR PREPARING THE SAME

BACKGROUND OF THE PRESENT INVENTION

The present invention relates to fish oil having decreased fish odor and to a method for preparing the fish oil. The present invention, in particular, relates to fish oil having decreased fish odor and containing a large amount of highly unsaturated fatty acids such as docosahexaenoic acid (DHA) and eicosapentaenoic acid (EPA) and to a method for preparing the fish oil.

Fat is one of the major three nutrients in range with protein and carbohydrate and plays an important roll as an energy source. As for Japanese people, the rate of fat energy in all energy in diet reaches to about 25% at present. The fat is also an important component constituting organism, and there are many reports that various symptom and disorder appear when fat digestion from diet is lacked.

In addition, fat has a structure in which three molecules of fatty acids are ester-bonded to a glycerol skeleton and the properties and rolls of fats in organisms depend largely on species and combination of the fatty acids. Among the fatty acids, there are many highly unsaturated fatty acids which themselves or whose metabolites show useful physiological functions in organisms. Since, for example, the lack of linoleic acid or α-linolenic acid results in symptoms such as dermal disorder, decrement of anagenetic power, increase of sensitivity to infection and these fatty acids can not be synthesized in organisms and they must be ingested from diet, they are determined to be essential fatty acids.

DHA and EPA, in range with these essential fatty acids, are seemed to be useful for prophylaxis and therapy of circulatory system diseases and another geriatric diseases, and thus they are highly unsaturated fatty acids which has been given attention in recent years. In particular, actions to blood circulation system such as platelet aggregation decrease, hemocholesterol decrease, blood sugar decrease, liver neutral fat decrease, prophylaxis and therapy effects on rheumatism, actions to decrease the development rate of various malignant tumor, immunological regulatory actions to atopy, asthma, pollinosis, further as actions which is given attention recently, actions to nervous system such as development and improvement of learning function and memory, inhibition of dementia, inhibition of increase or decrease of optesthesia, are reported ('Development and Application of Functional Lipid', supervised by K. Sato et al, CMC 'Shokuhin to Kaihatsu' October, 1992, published by Kenko Sangyo Shinbunsha).

The DHA and EPA of which various physiological functions have been reported, exist in fats of many fish species, whales, and marine products. The contents thereof are different depending on the fish species or whole species, on their regions, or on place or season of catch. It is known that a large amount of EPA is contained in fat of small-sized fish such as sardine, mackerel and horse mackerel, and a large amount of DHA is contained in fat of large-sized fish such as skipjack, tuna, marlin, amberjack and shark (Yushi Kagaku Binran 3rd Ed.).

Among these fish species and whale species, sardine, mackerel, skipjack and tuna contain a large amounts of highly unsaturated fatty acids such as DHA and EPA in their body fat. In addition, in orbital fat which exists in the back region of eyeball of skipjack or tuna, an extremely large amount of highly unsaturated fatty acid such as DHA is existing.

Generally, these fish oil containing large amounts of DHA and EPA is obtained by squeezing oil from whole fish body or part of fish body and removing water-soluble fraction from the oil by an operation such as decantation and centrifugation. Further, a highly unsaturated fatty acids such as DHA and EPA may be concentrated by an operation such as fractionation or wintering to increase the amounts thereof.

Although flavor is an important factor for food material, fish oil has unique odor (fish odor) and thus the utilization as food material is limited. At present, as to fish odor, it is attempted to remove it by adsorption to active carbon, active clay, diatomite and the like, molecular distillation or steam distillation. However, even if these deodorizing treatment is carried out, when the deodorized fish oil or food containing the oil is preserved, fish odor is produced during the preservation. These fish odors are produced by oxidative deterioration of highly unsaturated fatty acids such as DHA and EPA. It is reported that the odor components are aldehydes such as nonadienal, decatrienal, hexenal and heptenal or ketones such as octadienone (karahadian and Linsay, J. of Am. oil Chemists' Society, vol. 66, No. 7, p. 953, 1989). Therefore, when fish oil is utilized as a food material, there exits a big problem of production of fish odor and thus removal of these odor components and inhibition of production have been important technical subjects.

As to sardine oil, mackerel oil, skipjack oil, tuna oil, skipjack orbital fat and tuna orbital fat, the removal or inhibition of production of these odor components have been important subjects, and the removal of fish odor by adsorption to active carbon, active clay, diatomite and the like, molecular distillation or steam distillation have been attempted. However, since the above fish oil treated by these methods also produces fish odor during preservation, it is indispensable at present to control oxidative deterioration using a high amount of vitamin E, ascorbic acid and derivatives thereof, lecithin or another many kinds of antioxidants.

On the other hand, hydrogenation of oil is a typical technique concerning a production of processed oil as well as interesterification and fractionation. A hardened oil obtained by hydrogenation is a useful processed oil in range with fractionated oil and interesterified oil, and it plays an important roll in the production of oil foods. The hydrogenation is carried out usually at a reaction temperature in the range from 120° to 200° C. under hydrogen atmosphere in the existence of catalyst with stirring liquid oil. At the time, the hydrogen pressure is in the range from normal pressure to about 5 $kg/cm^2$. As a catalyst, nickel catalyst such as reduced nickel, nickel formate, Raney nickel and nickel borate is often used. By the hydrogenation, C-C double bond in a fatty acid consisting oil is hydrogenated.

The hardened oil obtained by hydrogenation has the following characteristics:

(1) Melting point of oil increases and thus it may be used as a plastic oil:

(2) Double bonds (unsaturated bonds) decrease and thus oxidative stability of oil is improved;

(3) With a selective hydrogenation, a solid fat content (SFC) vs temperature curve is changed to a sharp vertical curve, and with mixing with another oil or fractionation, it changed to an oil having good aptitude to food such as chocolate, margarine and shortening.

Hitherto, it has been carried out to improve oxidative stability to inhibit the fish odor production by hydrogenating fish oil to obtain hardened fish oil, and which is a conventional method in order to utilize fish oil as food material. It is described that as a food material a hardened fish oil having an increased melting point to 20° to 45° C., preferably to 35°

C. or more is easy to use. ('Yushi, Yuryo handbook', supervised by A. Yoshiro, published by Saiwai shobo).

However, highly unsaturated fatty acids such as DHA and EPA contained in fish oil will disappear by hydrogenation of the fish oil. Thus hardened fish oils which are available at present contain no highly unsaturated fatty acids such as DHA and EPA, or contain little these fatty acids. These has been no report about an attempt to prepare fish oil in which a large amount of highly unsaturated fatty acids such as DHA and EPA are remained and the fish odor production is inhibited by hydrogenation and which has no organoleptic problem.

SUMMARY OF THE INVENTION

The present invention was made in view of the above mentioned problems and the purpose of the present invention is to provide a method for preparing fish oil which produces decreased fish odor and contains a high amount of highly unsaturated fatty acids such as DHA and EPA, by under non-selective conditions hydrogenating fish oil, which may be a useful food material owing to its many physiological functions but which can not be utilized easily owing to its specific odor or whose utilization is limited, and the fish oil which may be prepared by the method.

Another object of the present invention is to provide sardine oil having decreased fish odor and containing a high amount of highly unsaturated fatty acids such as DHA and EPA and a method for preparing the sardine oil Still another object of the present invention is to provide mackerel oil having decreased fish odor and containing a high amount of highly unsaturated fatty acids such as DHA and EPA and a method for preparing the mackerel oil.

Still another object of the present invention is to provide skipjack oil having decreased fish odor and containing a high amount of highly unsaturated fatty acids such as DHA and EPA and a method for preparing the skipjack oil.

Still another object of the present invention is to provide tuna oil having decreased fish odor and containing a high amount of highly unsaturated fatty acids such as DHA and EPA and a method for preparing the tuna oil.

Still another object of the present invention is to provide skipjack orbital fat having decreased fish odor and containing a high amount of highly unsaturated fatty acids such as DHA and EPA and a method for preparing the skipjack orbital fat.

Still another object of the present invention is to provide a tuna orbital fat having decreased fish odor and containing a high amount of highly unsaturated fatty acids such as DHA and EPA and a method for preparing the tuna orbital fat.

DETAILED DESCRIPTION OF THE INVENTION

The present invention in order to attain the above objects comprises a method for preparing fish oil having decreased fish odor and containing a high amount of highly unsaturated fatty acids such as DHA and EPA, which comprises slightly hydrogenating fish oil to have a decrease rate of iodine value of 15% or less and a decrease rate of highly unsaturated fatty acid of 33% or less, and the fish oil which may be prepared by the method. The term 'slight hydrogenation' as used herein means a hydrogenation which results in decrease rate of iodine value of 15% or less.

The present invention also comprises a method for preparing fish oil having decreased fish odor and containing a high amount of highly unsaturated fatty acids such as DHA and EPA, which comprises slightly hydrogenating fish oil under a predetermined non-selective conditions, and the fish oil prepared by the method.

The non-selective conditions of the slight hydrogenation according to the present invention is:

(1) an amount of catalyst used in the hydrogenation is 0.05% by weight or more to an amount of the fish oil;

(2) hydrogen pressure in gaseous phase at the beginning of hydrogenation is 3 $kg/cm^2$ or more;

(3) reaction temperature of the hydrogenation is in the range from 90° to 150° C.;

(4) reaction time of the hydrogenation is in the range from 5 to 30 minutes.

The present invention also comprises sardine oil having the following characteristics and a method for preparing the oil:

(1) a concentration of DHA contained in fatty acid residue of the oil is in the range from 1 to 13%;

(2) a concentration of EPA contained in fatty acid residue of the oil is in the range from 3 to 18%;

(3) the trans-isomer content is 4% or more.

The present invention also comprises mackerel oil having the following characteristics and a method for preparing the oil:

(1) a concentration of DHA contained in fatty acid residue of the oil is in the range from 1 to 13%;

(2) a concentration of EPA contained in fatty acid residue of the oil is in the range from 3 to 18%;

(3) the trans-isomer content is 4% or more.

The present invention also comprises skipjack oil having the following characteristics and a method for preparing the oil:

(1) a concentration of DHA contained in fatty acid residue of the oil is in the range from 15 to 25%;

(2) a concentration of EPA contained in fatty acid residue of the oil is in the range from 1 to 10%;

(3) the trans-isomer content is 4% or more.

The present invention also comprises tuna oil having the following characteristics and a method for preparing the oil:

(1) a concentration of DHA contained in fatty acid residue of the oil is in the range from 15 to 25%;

(2) a concentration of EPA contained in fatty acid residue of the oil is in the range from 1 to 10%;

(3) the trans-isomer content is 4% or more.

The present invention also comprises skipjack orbital fat having the following characteristics and a method for preparing the oil:

(1) a concentration of DHA contained in fatty acid residue of the oil is in the range from 25 to 38%;

(2) a concentration of EPA contained in fatty acid residue of the oil is in the range from 2 to 8%;

(3) the trans-isomer content is 4% or more.

The present invention also comprises tuna orbital fat having the following characteristics and a method for preparing the oil:

(1) a concentration of DHA contained in fatty acid residue of the oil is in the range from 25 to 38%;

(2) a concentration of EPA contained in fatty acid residue of the oil is in the range from 2 to 8%;

(3) the trans-isomer content is 4% or more.

Since the slightly hydrogenated fish oil obtained by the method of the present invention produces little fish odor having a undesirable organoleptic effect and disappearance of highly unsaturated fatty acids such as DHA and EPA in fish oil is inhibited at the minimum, the fish oil is suitable for the use as food material and may be applied to medical supplies. Further it is possible to reinforce the decreasing effect of fish odor by using the slightly hydrogenated fish oil obtained by the method of the present invention together with an antioxidant, and by combining with another purified fat, and such fish oil may be used as a good-taste and stable oil The fish oil used as raw material in the present invention is collected from fish bodies of small-sized or middle-sized blueback fish such as sardine, horse mackerel, mackerel or big-sized blueback fish such as tuna, skipjack, marlin. However the fish oil as a raw material is not limited thereto and may be collected from shark, whale, cuttlefish and the like. Further the fish oil used as raw material may be collected from parts of fish body such as internal organs e.g. liver, head and eye and the like not from whole fish body. In the present invention, the fish oil collected from sardine, mackerel, tuna, skipjack and further tuna orbital fat or tuna orbital fat is most preferable.

Sardine generally means spotlined sardine of Clupeidae and round herring of Dussumieriinae, Japanese anchovy of Engraulidae and related species thereof but scientifically spotlined sardine is classified into Sardinops genus, round herring is classified into Etrumeus genus, and Japanese anchovy is classified into Engraulis genus. Sardine is distributed in all over the world ocean, and is called Sardine, Pilchard, Anchovy, Clupeoid, Herring-like fishes and the like, depending on the species. As for the sardine, approximately 10% of fat is occupied in fish body weight and the sardine contains a large amount of highly unsaturated fatty acids, i.e., it has 4 to 14% of DHA and 10 to 23% of EPA in body fat. The sardine has been considered to be a useful fish from old times as a highly available fish. Sardine is marketed and eaten by processing into Namasu (a dish of fish and vegetables seasoned with vinegar); baking, grilling, broiling; treating for preservation such as into a salted food, a food preserved in sake lees, a food preserved in malted rice, a salted and dried food; or processing into canned or bottled food in oil. In addition, sardine is used as feed or fertilizer. The production quantity of sardine is large and the catch quantity of sardine in Japan is about 2,720,000 ton (1980) and, addition to it, about 30,000 ton of sardine is imported at present ('Shokuhin, Seisan, Yunyu, Shohi, 1993' edited by Shokuhin Ryutsu Kenkyuukai (1993)).

Mackerel generally is a generic name of Lateolabrax japonicus Scombridae 15,48 and it primarily means chub mackerel and spotted mackerel. Mackerel is distributed in all regions of tropical and subtropical ocean areas, and it has a Latin name of Scomber, and is called mackerel (English), maquereau (French), makrele (German) and makreel (Dutch) and is an object of fishery. As for the mackerel, approximately 10 to 15% of fat is occupied in fish body weight and the mackerel contains a large amount of highly unsaturated fatty acids, i.e., it has 4 to 18% of DHA and 7 to 20% of EPA in body fat. The mackerel has a nature of making an excursion in a large group, and thus it has been an important edible fish since old time in Europe, Mediterranean area and Japan and the like. The domestic production of mackerel in Japan exceeded 1,000,000 ton (1980) and after that it has been decreasing but it keeps about 300,000 ton (1992). The import quantity of mackerel is also large and about 140,000 ton of mackerel is imported from Norway and other countries at present ('Shokuhin, Seisan, Yunyu, Shohi, 1993', edited by Shokuhin Ryutsu Kenkyuukai (1993)).

Skipjack generally has a scientific name of Lateolabrax japonicus Scombridae Katsuwonus pelamis 1 and has a Latin name of Katsuwonus. The skipjack contains a large amount of highly unsaturated fatty acids, i.e., it has 20 to 25% of DHA and 5 to 10% of EPA in body fat. The skipjack is distributed in all regions of tropical and temperate oceans areas and is called Skipjack, Bonito (English), Bonite, Listao (French) and Bonito (German) and is an object of fishery. The catch quantity of skipjack in Japan is about 320,000 ton (1992) and further about 30,000 ton of tuna is imported at present ('Shokuhin, Seisan, Yunyu, Shohi, 1993', edited by Shokuhin Ryutsu Kenkyuukai (1993)).

Tuna generally has a scientific name of Lateolabrax japonicus Scombridae Thunnus 7 and has a Latin name of Thunnus. Tuna contains a large amount of highly unsaturated fatty acids, i.e., it has 20 to 30% of DHA and 3 to 10% of EPA in body fat. The tuna is distributed in all regions of tropical and temperate oceans area and is called Tuna (English), Thon (French) and Thun (German) and the like and is an object of fishery. The catch quantity of tuna in Japan is about 340,000 ton (1992) and further about 250,000 ton of tuna is imported at present ('Shokuhin, Seisan, Yunyu, Shohi, 1993', edited by Shokuhin Ryutsu Kenkyuukai (1993)). In particular, the catch quantities and import quantities of bigeye tuna and yellowfin tuna are both large.

Highly unsaturated fatty acids, especially DHA exist in a very high amount in orbital fat which is the fat existing in back position of skipjack and tuna eyeballs. The highly unsaturated fatty acid content in these orbital fat varies depending upon fish species, fishery sea area and fishery season, but DHA exists in an amount in the range from 30 to 40% and EPA exists in an amount in the range from 4 to 10% in skipjack orbital fat and tuna orbital fat. The orbital fat collected from skipjack or tuna may be obtained by removing water-soluble fraction from oil by a centrifugation after acid treatment and treatments such as degumming and deacidification.

In the present invention, these fish oils as raw materials may be directly slightly hydrogenated. However, it is desirable to purify these fish oils used for slight-hydrogenation as much as possible since complex lipids typically exemplified by phospho lipids or proteins existing in fish oils poison the catalyst used in the slight-hydrogenation and deteriorate the catalytic activity to inhibit the slight-hydrogenation progress.

In the present invention, a fish oil as raw material and a catalyst for hydrogenation may be supplied into a reaction vessel to carry out a slight-hydrogenation reaction.

As the catalyst for hydrogenation, a reduced catalyst may be used, and it may include a nickel catalyst having nickel as main constituent element such as reduced nickel, nickel formate, Raney nickel, nickel borate; a metal catalyst formed from platinum, palladium, iron, copper and the like; and a hydrogen storage (occlusion) alloy such as lanthanum series alloy and calcium series alloy. They may be selected for use depending on the catalytic activity and the reaction condition desired. In the present invention, it is preferable, in particular, that one, two or more nickel catalysts may be preferably selected and used.

These catalysts are preferably used in an amount of 0.05% by weight or more to oil in order to proceed non-selective slight-hydrogenation in the present invention although these catalysts are used in an amount of 0.02 to 0.20% by weight to oils in conventional hydrogenation.

A reaction vessel which is resistant to pressure and is equipped with stirring device is preferably used, and the shape or size of a vessel is not limited. In addition, batch type reaction vessel may be used and continuous type reaction vessel may be used.

In the present invention, the fish oil and catalyst supplied to the reaction vessel, are deaerated and dehydrated sufficiently by reducing pressure preferably to 5 torr or less with stirring and then these are preferably heated to a predetermined reaction temperature with keeping them at the reduced pressure. However, if the fish oil used is already sufficiently dehydrated, the reduction of pressure is not indispensable. The fish oil and catalyst are not necessarily filled into a reaction vessel at the same time and the catalyst may be filled into a reaction vessel after the fish oil is filled into it and it reaches the predetermined conditions. In addition, the opposite operation may be made.

Then after the fish oil and catalyst reach the predetermined temperature, hydrogen gas is supplied into the reaction vessel to start slight-hydrogenation. At the time, the hydrogen pressure of gaseous phase in the reaction vessel is preferably set at 3 $kg/cm^2$ or more. The hydrogen pressure is preferably kept while the slight-hydrogenation is carried out. As a reaction temperature, it is preferable to keep a temperature at which the catalyst exhibits its activity and a temperature as low as possible. These optimum reaction temperature is determined depending on the catalyst species but is preferably in the range from 90° to 150° C. when a nickel catalyst is used.

In the present invention, after a predetermined time passes from the beginning of the hydrogenation, the stirring is stopped and hydrogen gas is removed from the reaction vessel to stop the hydrogenation reaction. If a reaction vessel in which a rapid temperature change operation may be made, the hydrogenation reaction may be stopped by cooling the fish oil temperature rapidly to 50° C. or less, preferably to 10° C. or less. In the present invention, the reaction time is preferably in the range from 5 to 30 minutes in order to keep the extent of the hydrogenation in the range of slight-hydrogenation.

Then when the slight-hydrogenated fish oil is taken out from the reaction vessel, the fish oil is most preferably cooled to 20° C. or less in order to inhibit oxidative deterioration of the slight-hydrogenated fish oil. An adsorbent such as active clay may be added to the slight-hydrogenated fish oil which is thus taken out from the reaction vessel, and the adsorbent and the fish oil are stirred. The adsorbent may be used in an amount of 1 to 5% by weight to the fish oil but it is not limited thereto. As the adsorbent, diatomite may be used besides active clay, and silica.gel and florisil and the like may be mixed with active clay or diatomite and may be used. Then the catalyst and the adsorbent are removed by filtration using filterpress and the like to collect the slight-hydrogenated fish oil. On the other hand, vacuum drying is conveniently made to remove water but freeze drying may be made and dehydrating agent may be used. Further, depending on the necessities, deodorizing treatments such as steam distillation may be made on the slight-hydrogenated fish oil. The slight-hydrogenated fish oil having reduced fish odor may be stored in refrigerator after adding an antioxidant to it and blowing an inactive gas into it.

The fish oil having decreased fish odor of the present invention may be used by mixing with another food oil, depending on the necessities. In addition, after a fish oil as a raw material is mixed with another food oil, the method for preparing the fish oil having decreased fish odor of the present invention may be carried out to obtain the fish oil having decreased fish odor of the present invention.

By the above mentioned slight-hydrogenation operation, fish odor components or precursors thereof are reduced, isomerized or decomposed to be converted into a chemical components producing no fish odor. Therefore, since the slight-hydrogenated fish oil of the present invention has no fish odor and production of fish odor during storage is inhibited, the fish oil of the present invention has no organoleptic problem. Further, in the slight-hydrogenated fish oil of the present invention, disappearance of highly unsaturated fatty acids such as DHA and EPA is little and these acids remain in the fish oil in high amounts. Further, the decrease of iodine value and increase of melting point are small. Namely, in the slight-hydrogenated fish oil obtained in the present invention, the decrease rate of iodine value from fish oil as raw material is preferably 15% or less but most preferably in the range from 5 to 10% in order to exhibit the effect of decreasing fish odor by the present invention effectively and to inhibit the disappearance of highly unsaturated fatty acids such as DHA and EPA.

The sardine oil or mackerel oil having decreased fish odor which may be obtained by the method of the present invention each contains 1 to 13% of DHA in fatty acid residue and 3 to 18% of EPA in fatty acid residue. The trans-isomer content of each oil is 4% or more and the each oil was changed to sufficiently stabilized fish oil by the present method. On the other hand, usual sardine oil or mackerel oil contains little positional isomer and the trans-isomer content is 1 to 2% or less.

The skipjack oil or tuna oil having decreased fish odor obtained by the method of the present invention contains 15 to 25% of DHA in fatty acid residue and 1 to 10% of EPA in fatty acid residue. The trans-isomer content of each oil is 4% or more and the each oil was changed to sufficiently stabilized fish oil. On the other hand, usual skipjack oil or tuna oil contains little positional isomer and the trans-isomer content is 1 to 2% or less.

The skipjack orbital fat or tuna orbital fat having decreased fish odor obtained by the method of the present invention contains 25 to 38% of DHA in fatty acid residue and 2 to 8% of EPA In fatty acid residue. Further, the trans-isomer content of the each orbital fat is 4% or more and the each fat was changed to sufficiently stabilized fish oil. On the other hand, usual skipjack orbital fat or tuna orbital fat contains little positional isomer and the trans-isomer content is 1 to 2% or less.

These measurements of trans-isomer content was carried out in accordance with Standard Oil Analysis Test method 2.4.24 established by Nihon Yukagaku Kyokai, or with Official and Tentative Methods of the American Oil Chemists' Society, Official Method Cd 14-61.

These fish oils of the present invention may be used alone or may be used mixing with another one or more fish oils of the present invention.

Further, by our preservation test and organoleptic evaluation on the each fish oil having decreased fish odor of the present invention, it was confirmed that the fish oils of the present invention produce little fish odor and are excellent also in flavor. Therefore, the fish oil having decreased fish odor of the present invention is suitable for the use as food material and is useful as raw material for any type of foods for example beverages such as milk shake, coffee beverages and lactic acid beverages; desserts such as ice cream, jelly, mousse, yogurt; Miso, meat product, fish meat product; milk products such as powder milk, cheese food, fat spread; or baby food. In addition, the fish oil of the present invention may be used as a material for medical products.

By using the fish oil having decreased fish odor of the present invention, the amount of antioxidant which has been used to maintain the flavor-stability, may be decreased.

The present invention will be described below in more detail by referring to the following examples.

EXAMPLE 1

600 g of purified sardine oil (iodine value: 162, DHA: 8.4%, EPA: 15.2%) was filled into a 1L reaction vessel, and 0.6 g (0.1% by weight) of Raney nickel catalyst was added to it. Then, after deaerating and dehydrating it to have a pressure of 5 torr or less with stirring, a hydrogenation reaction was carried out under hydrogen atmosphere of 4 kg/cm$^2$ at 100° C. for 30 minutes. Then the hydrogenation reaction was stopped by removing hydrogen gas from the reaction vessel, and after cooling the oil to 20° C. or less, the oil was treated with active clay to have 515 g of slightly hydrogenated sardine oil. Iodine value of the slightly hydrogenated sardine oil was 149, contents of DHA and EPA thereof were 6.8% and 12.2%, respectively.

A preservation test was carried out on the purified sardine oil used as a raw material and the slightly hydrogenated sardine oil obtained in the example.

50 g of each oil was filled into a 100 ml of glass vessel having a cap, 30 mg of tocopherol was added to each oil as an antioxidant, and they were stored in a temperature-controlled oven which was kept at 30°±1° C. and was protected from light to carry out preservation test. An organoleptic evaluation was made by ten well-trained professional panels using the following evaluation standards on the fish odor strength and preferability listed in Table 1.

TABLE 1

| Evaluation | Fish Odor Strength | Preferability |
|---|---|---|
| 0 | feel not at all | extremely bad |
| 1 | feel very little | bad |
| 2 | feel slightly | a little bad |
| 3 | feel odor | not bad and not good |
| 4 | feel a little strongly | good |
| 5 | feel strongly | extremely good |

The results will be shown in Table 2. An average of the evaluation points made by all panels was shown as an organoleptic evaluation point.

TABLE 2

| | Fish Odor Strength | | Preferability | |
|---|---|---|---|---|
| Oil | 0 day | 7th day | 0 day | 7th day |
| Purified Sardine Oil | 1.5 | 3.2 | 3.9 | 2.6 |
| Sardine Oil of the Present Invention | 1.0 | 2.5 | 4.3 | 3.1 |

As apparent from the above results, the sardine oil of the present invention had low fish odor at 0 day of preservation compared with the purified sardine oil. Further, even at 7th day of preservation, the sardine oil of the present invention had low fish odor and the production of fish odor during preservation was inhibited. In addition, the sardine oil of the present invention had always high evaluation points of preferability reflecting the behaviors of the fish odor strength.

EXAMPLE 2

2 kg of purified sardine oil (DHA: 6.5%, EPA: 19.34, trans-isomer content: 0.8%) was filled into a 4L reaction vessel, and 1.5 g (0.075% by weight) of reduced nickel catalyst was added to it. Then, after deaerating and dehydrating it to have a pressure of 5 torr or less with stirring, hydrogenation reaction was carried out under hydrogen atmosphere of 3 kg/cm$^2$ at 130° C. for 15 minutes. Then the hydrogenation reaction was stopped by removing hydrogen gas from the reaction vessel and after cooling the oil to 20° C. or less, it was treated with active clay to have 1.75 kg of sardine oil having decreased fish odor of the present invention. The DHA content of the sardine oil obtained was 3.2%, the EPA content was 14.9% and the trans-isomer content was 4.2%.

A preservation test was carried out on the purified sardine oil used as a raw material and the sardine oil obtained in the example.

50 g of each sardine oil was filled into a 100 ml of glass vessel having a cap, 15 mg of tocopherol was added to each oil as an antioxidant, and they were stored in an oven kept at 50°±1° C., to make a preservation test. An organoleptic evaluation was carried out in the same manner as described in Example 1, according to the standards shown in Table 1. The results will be shown in Table 3.

TABLE 3

| | Fish Odor Strength | | Preferability | |
|---|---|---|---|---|
| Oil | 0 day | 7th day | 0 day | 7th day |
| Purified Sardine Oil | 1.5 | 3.8 | 3.9 | 1.8 |
| Sardine Oil of the Present Invention | 1.0 | 1.9 | 4.2 | 3.6 |

As apparent from the above results, the sardine oil of the present invention had weak fish odor from the 0 day of preservation compared with the purified sardine oil. In addition, even at 7th day of preservation, the production of fish odor in the sardine oil of the present invention was inhibited and the evaluation point of preferability was high.

EXAMPLE 3

500 g of purified sardine oil (DHA: 6.5%, EPA: 19.3%, trans-isomer content: 0.8%) was filled into a 1L reaction vessel, and 0.25 g (0.050% by weight) of Raney nickel catalyst was added to the oil. Then, after deaerating and dehydrating it to have a pressure of 5 torr or less with stirring, and hydrogenation reaction was carried out under hydrogen atmosphere of 4 kg/cm$^2$ at 110° C. for 10 minutes. Then the hydrogenation reaction was stopped by removing hydrogen gas from the reaction vessel, and after cooling the oil to 20° C. or less, the oil was treated with active clay to have 432 g of sardine oil having decreased fish odor of the present invention. The DHA content of the sardine oil thus obtained was 3.9%, the EPA content was 11.4% and the trans-isomer content was 8.8%.

Then a preservation test was carried out on the purified sardine oil used as a raw material and the sardine oil obtained in the example. The preservation test was made by a forced-deterioration test in the same manner as described in Example 2 except that the temperature of the oven was 30°±1° C., and organoleptic evaluation was made. The results will be shown in Table 4.

TABLE 4

| | Fish Odor Strength | | Preferability | |
|---|---|---|---|---|
| Oil | 0 day | 7th day | 0 day | 7th day |
| Purified Sardine Oil | 1.4 | 4.1 | 4.0 | 2.0 |
| Sardine Oil of the Present Invention | 0.9 | 2.5 | 4.3 | 3.4 |

As apparent from the above results, the sardine oil of the present invention had weak fish odor from the 0 day of preservation compared with the purified sardine oil. In addition, even at 7th day of preservation, the production of fish odor in the sardine oil of the present invention was inhibited and the evaluation point of preferability was high.

EXAMPLE 4

200 g of purified sardine oil (DHA: 13.3%, EPA: 20.6%, trans-isomer content: 0.8%), which had been deaerated and dehydrated sufficiently, was dissolved in 500 ml of hexane and filled into a 2L reaction vessel, and 10 g of palladium catalyst (Pd—$CaCO_3$) was added. Then hydrogenation reaction was carried out at a hydrogen atmosphere of 1 kg/cm$^2$ at room temperature (25° C.) for one hour. Then after taking out the sardine oil from the reaction vessel and removing the catalyst by filtration, the oil was dried under reduced pressure to remove hexane and was treated with active clay to have 148 g of sardine oil having decreased fish odor of the present invention. The DHA content of the sardine oil thus obtained was 6.2%, the EPA content was 15.3% and the trans-isomer content was 9.04.

Then the purified sardine oil used as a raw material and the sardine oil obtained in the example were each mixed with soybean oil and a preservation test was carried out. The each sardine oil was mixed with soybean oil to have DHA content and EPA content in the mixed oil of 3.0%, respectively. The preservation test and organoleptic evaluation were made by a forced-deterioration test in the same manner as described in Example 2. The results will be shown in Table 5.

TABLE 5

| | Fish Odor Strength | | Preferability | |
|---|---|---|---|---|
| Oil | 0 day | 14th day | 0 day | 14th day |
| Purified Sardine Oil | 1.4 | 3.2 | 3.8 | 2.3 |
| Sardine Oil of the Present Invention | 1.0 | 2.2 | 4.1 | 2.9 |

As apparent from the above results, the mixed oil containing the sardine oil of the present invention had weak fish odor from the 0 day of preservation compared with the mixed oil containing the purified sardine oil and had high evaluation point of the preferability. In addition, even at 14th day of preservation, the production of fish odor in the mixed oil containing the sardine oil of the present invention was inhibited and the evaluation point of preferability was high.

EXAMPLE 5

500 g of purified mackerel oil (DHA content: 12.8%, EPA content: 16.4%, trans-isomer content: 1.8%) was filled into a 1L reaction vessel, and 0.375 g (0.075% by weight) of reduced nickel catalyst was added to the oil. After deaerating and dehydrating it so as to have a pressure of 5 torr or less with stirring, a hydrogenation reaction was carried out under hydrogen atmosphere of 3 kg/cm$^2$ at 130° C. for twenty minutes. Then hydrogen gas was removed from the reaction vessel to stop the hydrogenation reaction, and after cooling it to 20° C. or less, the oil was treated with active clay to obtain 373 g of mackerel oil having decreased fish odor of the present invention. The DHA content of the mackerel oil thus obtained was 8.1%, the EPA content was 13.9% and the trans-isomer content was 6.2%.

Then a preservation test was made on the purified mackerel oil used as a raw material and the mackerel oil obtained in the example. Namely, the preservation test by a forced-deterioration test and organoleptic evaluation were made in the same manner as described in Example 2. The results will be shown in Table 6.

TABLE 6

| | Fish Odor Strength | | Preferability | |
|---|---|---|---|---|
| Oil | 0 day | 3rd day | 0 day | 3rd day |
| Purified Mackerel Oil | 1.4 | 3.7 | 3.6 | 1.8 |
| Mackerel Oil of the Present Invention | 1.1 | 2.0 | 4.0 | 3.4 |

As apparent from the above results, the mackerel oil of the present invention had weak fish odor from the 0 day of preservation compared with the purified mackerel oil and had high evaluation point of the preferability. In addition, even at 3rd day of preservation, the production of fish odor in the mackerel oil of the present invention was inhibited and the evaluation point of preferability was high.

EXAMPLE 6

500 g of mixed oil (DHA content: 8.84, EPA content: 18.7%, trans-isomer content: 1.0%), in which purified sardine oil (DHA content: 6.5%, EPA content: 19.3%, trans-isomer content: 0.8%) and purified mackerel oil (DHA content: 12.8%, EPA content: 16.4%, trans-isomer: 1.8%) were mixed in the ratio of 80:20 by weight, was filled into a 1L reaction vessel, and 0.5 g (0.10% by weight) of reduced nickel catalyst was added to the mixed oil. After deaerating and dehydrating the mixed oil so as to have a pressure of 5 torr or less with stirring, a hydrogenation reaction was carried out under hydrogen atmosphere of 3 kg/cm$^2$ at 130° C. for fifteen minutes. Then hydrogen gas was removed from the reaction vessel to stop the hydrogenation reaction, and after cooling it to 20° C. or less, the oil was treated with active clay to obtain 380 g of sardine and mackerel mixed oil having decreased fish odor of the present invention. The DHA content of the sardine and mackerel mixed oil thus obtained was 4.2%, the EPA content was 16.6% and the trans-isomer content was 5.9%.

Then a preservation test was made on the purified sardine and mackerel mixed oil used as a raw material and the sardine and mackerel oil obtained in the example. Namely, a preservation test made by a forced-deterioration test and organoleptic evaluation were made in the same manner as described in Example 2. The results will be shown in Table 7.

TABLE 7

| | Fish Odor Strength | | Preferability | |
|---|---|---|---|---|
| Oil | 0 day | 5th day | 0 day | 5th day |
| Purified Sardine/Mackerel Mixed Oil | 1.4 | 3.6 | 3.5 | 1.8 |
| Sardine/Mackerel Mixed Oil of the Present Invention | 1.1 | 2.2 | 3.9 | 3.2 |

As apparent from the above results, the mixed oil of the present invention had weak fish odor from the 0 day of preservation compared with the purified mixed oil and had high evaluation point of the preferability. In addition, even at 5th day of preservation, the production of fish odor in the mixed oil of the present invention was inhibited and the evaluation point of preferability was high.

EXAMPLE 7

2 kg of purified skipjack oil (iodine value: 182, DHA content: 23.5%, EPA content: 6.2%, trans-isomer content: 1.4%) was filled into a 4L reaction vessel, and 1.5 g (0.075% by weight) of reduced nickel catalyst was added to the oil. After deaerating and dehydrating it so as to have a pressure of 5 tort or less with stirring, a hydrogenation reaction was carried out at a hydrogen atmosphere of 3 kg/cm$^2$ at 130° C. for fifteen minutes. Then hydrogen gas was removed from the reaction vessel to stop the hydrogenation reaction, and after cooling it to 20° C. or less, the oil was treated with active clay to obtain 1.7 kg of slightly hydrogenated skipjack oil. The iodine value of the slightly hydrogenated skipjack oil thus obtained was 171, the DHA and EPA content was 17.2% and 5.2%, respectively.

Then a preservation test was made on the purified skipjack oil used as a raw material and the slightly hydrogenated skipjack oil obtained in the example. The preservation test by a forced-deterioration test and organoleptic test were made in the same manner as described in Example 2 except that the amount of tocopherol used was 30 ml. The results will be shown In Table 8.

TABLE 8

| | Fish Odor Strength | | Preferability | |
|---|---|---|---|---|
| Oil | 0 day | 3rd day | 0 day | 3rd day |
| Purified Skipjack Oil | 1.0 | 3.0 | 4.5 | 3.0 |
| Skipjack Oil of the Present Invention | 0.6 | 1.8 | 4.8 | 4.0 |

As apparent from the above results, the slightly hydrogenated skipjack oil of the present invention had weak fish odor at the 0 day of preservation compared with the purified skipjack oil and had high evaluation point of the preferability. In addition, even at 3rd day of preservation, the production of fish odor in the slightly hydrogenated skipjack oil of the present invention was inhibited and the evaluation point of preferability was high.

EXAMPLE 8

500 g of purified skipjack oil (DHA content: 23.5%, EPA content: 6.2%, trans-isomer content: 1.4%) was filled into a 1L reaction vessel, and 0.25 g (0.050% by weight) of Raney nickel catalyst was added to the oil. After deaerating and dehydrating it so as to have a pressure of 5 torr or less with stirring, a hydrogenation reaction was carried out under hydrogen atmosphere of 4 kg/cm$^2$ at 110° C. for ten minutes. Then hydrogen gas was removed from the reaction vessel to stop the hydrogenation reaction, and after cooling it to 20° C. or less, the oil was treated with active clay to obtain 440 g of skipjack oil having decreased fish odor of the present invention. The DHA content of the skipjack oil was 16.8%, the EPA content was 5.8%, and trans-isomer content was 6.8%.

Then a preservation test was made on the purified skipjack oil used as a raw material and the skipjack oil obtained in the example. Namely, the preservation test made by a forced-deterioration test and organoleptic evaluation were made in the same manner as described in Example 2, except that the oven temperature was 30°±1° C. The results will be shown in Table 9.

TABLE 9

| | Fish Odor Strength | | Preferability | |
|---|---|---|---|---|
| Oil | 0 day | 7th day | 0 day | 7th day |
| Purified Skipjack Oil | 1.0 | 4.1 | 4.5 | 2.0 |
| Skipjack Oil of the Present Invention | 0.6 | 2.0 | 4.8 | 3.9 |

As apparent from the above results, the skipjack oil of the present invention had weak fish odor from the 0 day of preservation compared with the purified skipjack oil and had high evaluation point of the preferability. In addition, even at 7th day of preservation, the production of fish odor in the skipjack oil of the present invention was inhibited and the evaluation point of preferability was high.

EXAMPLE 9

200 g of purified skipjack oil (DHA: 24.3%, EPA: 8.9%, trans-isomer content: 1.8%), which had been deaerated and dehydrated sufficiently, was dissolved in 500 ml of hexane and filled into a 2L reaction vessel, and 10 g of palladium catalyst (Pd—$CaCO_3$) was added to it. Then hydrogenation reaction was carried out under hydrogen atmosphere of 1 kg/cm$^2$ at room temperature (25° C.) for one hour. Then after taking out the skipjack oil from the reaction vessel and removing the catalyst by filtration, the oil was dried under reduced pressure to remove hexane and treated with active clay to have 156 g of skipjack oil having decreased fish odor of the present invention. The DHA content of the skipjack oil thus obtained was 19.2%, the EPA content was 7.2% and the trans-isomer content was 7.1%.

Then the purified skipjack oil used as a raw material and the skipjack oil obtained in the example were each mixed with soybean oil and a preservation test was carried out. The purified skipjack oil and the skipjack oil obtained in the example were each mixed with soybean oil to have DHA content and EPA content in each mixed oil of 3.0%, respectively. The preservation test by a forced-deterioration test and organoleptic evaluation were made in the same manner as described in Example 2. The results will be shown in Table 10.

TABLE 10

| Oil | Fish Odor Strength | | Preferability | |
|---|---|---|---|---|
| | 0 day | 18th day | 0 day | 18th day |
| Mixed Oil containing Purified Skipjack Oil | 1.0 | 3.2 | 4.3 | 2.4 |
| Mixed Oil containing Skipjack Oil of the Present Invention | 0.7 | 1.6 | 4.7 | 3.8 |

As apparent from the above results, the mixed oil containing the skipjack oil of the present invention had weak fish odor from the 0 day of preservation compared with the mixed oil containing the purified skipjack oil and had high evaluation point of the preferability. In addition, even at 18th day of preservation, the production of fish odor in the mixed oil containing the skipjack oil of the present invention was inhibited and the evaluation point of preferability was high.

EXAMPLE 10

2 kg of purified tuna oil (DHA content: 26.5%, EPA content: 7.2%, trans-isomer content: 1.1%) was filled into a 4L reaction vessel, and 1.5 g (0.075% by weight) of reduced nickel catalyst was added to the oil. After deaerating and dehydrating it so as to have a pressure of 5 torr or less with stirring, a hydrogenation reaction was carried out under hydrogen atmosphere of 3 kg/cm$^2$ at 130° C. for fifteen minutes. Then hydrogen gas was removed from the reaction vessel to stop the hydrogenation reaction and after cooling it to 20° C. or less, the oil was treated with active clay to obtain 1.7 kg of tuna oil having decreased fish odor of the present invention. The DHA content of the tuna oil was 21.2%, the EPA content was 6.2%, and trans-isomer content was 4.8%.

Then a preservation test was made on the purified tuna oil used as a raw material and the tuna oil obtained in the example. Namely, the preservation test by a forced-deterioration test and organoleptic test were made in the same manner as described in Example 2. The results will be shown in Table 11.

TABLE 11

| Oil | Fish Odor Strength | | Preferability | |
|---|---|---|---|---|
| | 0 day | 4th day | 0 day | 4th day |
| Purified Tuna Oil | 1.0 | 3.3 | 4.4 | 2.9 |
| Tuna Oil of the present Invention | 0.8 | 1.7 | 4.6 | 3.9 |

As apparent from the above results, the tuna oil of the present invention had weak fish odor from the 0 day of preservation compared with the purified tuna oil and had high evaluation point of the preferability. In addition, even at 4th day of preservation, the production of fish odor in the tuna oil of the present invention was inhibited and the evaluation point of preferability was high.

EXAMPLE 11

500 g of purified tuna oil (DHA content: 26.5%, EPA content: 7.2%, trans-isomer content: 1.1%) was filled into a 1L reaction vessel, and 0.25 g (0.050% by weight) of Raney nickel catalyst was added to the oil. After deaerating and dehydrating it so as to have a pressure of 5 torr or less with stirring, a hydrogenation reaction was carried out under hydrogen atmosphere of 4 kg/cm$^2$ at 110° C. for ten minutes. Then hydrogen gas was removed from the reaction vessel to stop the hydrogenation reaction. After cooling it to 20° C. or less, the oil was treated with active clay to obtain 435 g of tuna oil having decreased fish odor of the present invention. The DHA content of the tuna oil was 20.1%, the EPA content was 4.3%, and trans-isomer content was 6.5%.

Then a preservation test was made on the purified tuna oil used as a raw material and the tuna oil obtained in the example. Namely, the preservation test by a forced-deterioration test and organoleptic evaluation were carried out in the same manner as described in Example 2, except that the oven temperature was 30°±1° C. The results will be shown in Table 12.

TABLE 12

| Oil | Fish Odor Strength | | Preferability | |
|---|---|---|---|---|
| | 0 day | 10th day | 0 day | 10th day |
| Purified Tuna Oil | 1.0 | 4.0 | 4.5 | 2.5 |
| Tuna Oil of the Present Invention | 0.7 | 2.5 | 4.7 | 3.6 |

As apparent from the above results, the tuna oil of the present invention had weak fish odor from the 0 day of preservation compared with the purified tuna oil and had high evaluation point of the preferability. In addition, even at 10th day of preservation, the production of fish odor in the tuna oil of the present invention was inhibited and the evaluation point of preferability was high.

EXAMPLE 12

200 g of purified tuna oil (DHA: 26.5%, EPA: 7.2%, trans-isomer content: 1.1%), which had been deaerated and dehydrated sufficiently, was dissolved in 500 ml of hexane and filled into a 2L reaction vessel, and 10 g of palladium catalyst (Pd—$CaCO_3$) was added to it. Then hydrogenation reaction was carried out under hydrogen atmosphere of 1 kg/cm$^2$ at room temperature (25° C.) for one hour. Then after taking out the tuna oil from the reaction vessel and removing the catalyst by filtration, the oil was dried under reduced pressure to remove hexane and was treated with active clay to have 149 g of tuna oil having decreased fish odor of the present invention. The DHA content of the tuna oil thus obtained was 18.2%, the EPA content was 4.3% and the trans-isomer content was 7.3%.

Then the purified tuna oil used as a raw material and the tuna oil obtained in the example were each mixed with soybean oil and a preservation test was carried out. The purified tuna oil and the tuna oil obtained in the example were each mixed with soybean oil to have DHA content and EPA content in the mixed oils of 3.0%, respectively. The preservation test by a forced-deterioration test and organoleptic evaluation were made in the same manner as described In Example 2. The results will be shown In Table 13.

TABLE 13

| | Fish Odor Strength | | Preferability | |
|---|---|---|---|---|
| Oil | 0 day | 18th day | 0 day | 18th day |
| Mixed Oil containing Purified Tuna Oil | 1.0 | 2.9 | 4.3 | 2.8 |
| Mixed Oil containing Tuna Oil of the Present Invention | 0.6 | 1.5 | 4.6 | 3.6 |

As apparent from the above results, the mixed oil containing the tuna oil of the present invention had weak fish odor from the 0 day of preservation compared with the mixed oil containing the purified tuna oil, and it had high evaluation point of the preferability. In addition, even at 18th day of preservation, the production of fish odor in the mixed oil containing the tuna oil of the present invention was inhibited and the evaluation point of preferability was high.

EXAMPLE 13

2 kg of mixed oil (DHA content: 24.0%, EPA content: 7.6%, trans-isomer content: 1.4%), in which purified skipjack oil (DHA content: 22.5%, EPA content: 7.0%, trans-isomer content: 2.0%) and purified tuna oil (DHA content: 26.5%, EPA content: 8.6%, trans-isomer: 1.4%) were mixed in the ratio of 60:40 by weight, was filled into a 4L reaction vessel, and 1.5 g (0.075% by weight) of reduced nickel catalyst was added to the oil. After deaerating and dehydrating so as to have a pressure of 5 torr or less with stirring, a hydrogenation reaction was carried out under hydrogen atmosphere of 3 $kg/cm^2$ at 130° C. for fifteen minutes. Then hydrogen gas was removed from the reaction vessel to stop the hydrogenation reaction, and after cooling it to 20° C. or less, the mixed oil was treated with active clay to obtain 1.7 kg of skipjack and tuna mixed oil having decreased fish odor of the present invention. The DHA content of the skipjack and tuna mixed oil thus obtained was 18.6%, the EPA content was 6.3% and the trans-isomer content was 5.6%.

Then a preservation test was carried out on the purified mixed oil used as a raw material and the mixed oil obtained in the example. Corn oil was added to each above mixed oil to have DHA content in each mixed oil of 15%. Using each mixed oil, a preservation test by a forced-deterioration and organoleptic evaluation were made in the same manner as described in Example 2. The results will be shown in Table 14.

TABLE 14

| | Fish Odor Strength | | Preferability | |
|---|---|---|---|---|
| Oil | 0 day | 5th day | 0 day | 5th day |
| Mixed Oil containing the Purified oil | 1.0 | 3.2 | 4.4 | 2.9 |
| Mixed Oil containing the Oil of the Present Invention | 0.7 | 1.6 | 4.7 | 3.9 |

As apparent from the above results, the mixed oil of the present invention had weak fish odor from the 0 day of preservation compared with the mixed oil containing the purified oil, and it had high evaluation point of the preferability. In addition, even at 5th day of preservation, the production of fish odor in the mixed oil of the present invention was inhibited and the evaluation point of preferability was high.

EXAMPLE 14

500 g of purified tuna orbital fat (DHA content: 35.5%, EPA content: 7.2%, trans-isomer content: 1.4%) was filled into a 2L reaction vessel, and 0.50 g (0.10% by weight) of reduced nickel catalyst was added to the fat. After deaerating and dehydrating it so as to have a pressure of 5 torr or less with stirring, a hydrogenation reaction was carried out under hydrogen atmosphere of 3 $kg/cm^2$ at 130° C. for ten minutes. Then hydrogen gas was removed from the reaction vessel to stop the hydrogenation reaction. After cooling it to 20° C. or less, the fat was treated with active clay to obtain 378 g of tuna orbital fat having decreased fish odor of the present invention. The DHA content of the tuna orbital fat was 29.3%, the EPA content was 4.9%, and trans-isomer content was 6.3%.

Then a preservation test was made on the purified tuna orbital fat used as a raw material and the tuna orbital fat obtained in the example. The preservation by a forced-deterioration test and organoleptic evaluation were carried out in the same manner as described in Example 2, except that the tocopherol amount was 20 mg. The results will be shown in Table 15.

TABLE 15

| | Fish Odor Strength | | Preferability | |
|---|---|---|---|---|
| Oil | 0 day | 3rd day | 0 day | 3rd day |
| Purified Tuna Orbital Fat | 0.9 | 2.9 | 4.1 | 3.3 |
| Tuna Orbital Fat of the Present Invention | 0.6 | 1.5 | 4.5 | 3.9 |

As apparent from the above results, the tuna orbital fat of the present invention had weak fish odor from the 0 day of preservation compared with the purified tuna orbital fat, and it had high evaluation point of the preferability. In addition, even at 3rd day of preservation, the production of fish odor in the tuna orbital fat of the present invention was inhibited and the evaluation point of preferability was high.

EXAMPLE 15

300 g of purified skipjack orbital fat (DHA content: 36.5%, EPA content: 9.8%, trans-isomer content: 1.7%) was filled into a 1L reaction vessel, and 0.15 g (0.050% by weight) of Raney nickel catalyst was added to the fat. After deaerating and dehydrating it so as to have a pressure of 5 torr or less with stirring, a hydrogenation reaction was carried out under hydrogen atmosphere of 4 $kg/cm^2$ at 110° C. for 30 minutes. Then hydrogen gas was removed from the reaction vessel to stop the hydrogenation reaction, and after cooling it to 20° C. or less, the fat was treated with active clay to obtain 225 g of skipjack orbital fat having decreased fish odor of the present invention. The DHA content of the skipjack orbital fat was 30.3%, the EPA content was 7.6%, and trans-isomer content was 7.5%.

Then a preservation test was made on the purified skipjack orbital fat and the skipjack orbital fat obtained in the example. Namely, the preservation test by a forced-deterioration test and organoleptic evaluation were carried out in the same manner as described in Example 2, except that the tocopherol amount was 20 mg and the oven temperature was 30°±1° C. The results will be shown in Table 16.

TABLE 16

| | Fish Odor Strength | | Preferability | |
|---|---|---|---|---|
| Oil | 0 day | 10th day | 0 day | 10th day |
| Purified Skipjack Orbital Fat | 1.0 | 3.6 | 4.0 | 2.2 |
| Skipjack Orbital Fat of the Present Invention | 0.7 | 2.5 | 4.4 | 3.4 |

As apparent from the above results, the skipjack orbital fat of the present invention had weak fish odor from the 0 day of preservation compared with the purified skipjack orbital fat, and it had high evaluation point of the preferability. In addition, even at 10th day of preservation, the production of fish odor in the skipjack orbital fat of the present invention was inhibited and the evaluation point of preferability was high.

EXAMPLE 16

200 g of purified tuna orbital fat (DHA: 35.5%, EPA: 7.2%, trans-isomer content: 1.4%), which had been deaerated and dehydrated sufficiently, was dissolved in 500 ml of hexane and it was filled into a 2L reaction vessel, and 10 g of palladium catalyst (Pd—$CaCO_3$) was added to the fat. Then hydrogenation reaction was carried out under hydrogen atmosphere of 1 kg/cm$^2$ at room temperature (25° C.) for one hour. Then after taking out the tuna orbital fat from the reaction vessel and removing the catalyst by filtration, the orbital fat was dried under reduced pressure to remove hexane and was treated with active clay to have 149 g of tuna orbital fat having decreased fish odor of the present invention. The DHA content of the tuna orbital fat thus obtained was 32.5%, the EPA content was 3.3% and the trans-isomer content was 7.6%.

Then the purified tuna orbital fat used as a raw material and the tuna orbital fat obtained In the example were each mixed with soybean oil and a preservation test was carried out. The purified tuna orbital fat and the tuna orbital fat obtained in the example were each mixed with soybean oil to have DHA content and EPA content in each mixed oil of 10.0%, respectively. The preservation test by a forced-deterioration test and organoleptic evaluation were made in the same manner as described in Example 2 except that the amount of tocopherol was 20 mg. The results will be shown in Table 17.

TABLE 17

| | Fish Odor Strength | | Preferability | |
|---|---|---|---|---|
| Oil | 0 day | 14th day | 0 day | 14th day |
| Mixed Oil containing Purified Tuna Orbital Fat | 0.9 | 2.7 | 4.1 | 3.0 |

TABLE 17-continued

| | Fish Odor Strength | | Preferability | |
|---|---|---|---|---|
| Oil | 0 day | 14th day | 0 day | 14th day |
| Mixed Oil containing Tuna Orbital fat of the Present Invention | 0.6 | 1.6 | 4.4 | 3.6 |

As apparent from the above results, the tuna orbital fat of the present invention had weak fish odor from the 0 day of preservation compared with the purified tuna orbital fat, and it had high evaluation point of the preferability. In addition, even at 14th day of preservation, the production of fish odor in the tuna orbital fat of the present invention was inhibited and the evaluation point of preferability was high.

EXAMPLE 17

500 g of mixed fat (DHA content: 35.3%, EPA content: 7.8%, trans-isomer content: 1.8%), in which purified tuna orbital fat (DHA content: 36.0%, EPA content: 7.0%, trans-isomer content: 1.4%) and purified skipjack orbital fat (DHA content: 34.5%, EPA content: 8.9%, trans-isomer content: 1.8%) were mixed in the ratio of 50:50 by weight, was filled into a 1L reaction vessel, and 0.5 g (0.10% by weight) of reduced nickel catalyst was added to the fat. After deaerating and dehydrating it so as to have a pressure of 5 torr or less with stirring, a hydrogenation reaction was carried out under hydrogen atmosphere of 3 kg/cm$^2$ at 130° C. for fifteen minutes. Then hydrogen gas was removed from the reaction vessel to stop the hydrogenation reaction, and after cooling it to 20° C. or less, the mixed oil was treated with active clay to obtain 380 g of mixed tuna and skipjack orbital fat having decreased fish odor of the present invention. The DHA content of the mixed tuna and skipjack orbital fat thus obtained was 27.9%, the EPA content was 4.3% and the trans-isomer content was 6.8%.

Then a preservation test was made on the mixed purified tuna and skipjack orbital fat and the mixed tuna and skipjack orbital fat obtained in the example.

Namely, the preservation test by forced-deterioration test and organoleptic evaluation were made in the same manner as described in Example 2, except that 50 g of each oil prepared by adding corn oil to have DHA content of tuna and skipjack orbital fat of 25% and that the amount of tocopherol was 20 mg. The results will be shown in Table 18.

TABLE 18

| | Fish Odor Strength | | Preferability | |
|---|---|---|---|---|
| Oil | 0 day | 5th day | 0 day | 5th day |
| Mixed Purified Orbital Fat | 1.0 | 3.4 | 4.0 | 2.8 |
| Mixed Orbital Fat of the Present Invention | 0.6 | 1.8 | 4.3 | 3.7 |

As apparent from the above results, the mixed tuna and skipjack orbital fat of the present invention had weak fish odor from the 0 day of preservation compared with the mixed purified tuna and skipjack orbital fat, and it had high evaluation point of the preferability. In addition, even at 5th day of preservation, the production of fish odor in the mixed tuna and skipjack orbital fat of the present invention was inhibited and the evaluation point of preferability was high.

The fish oil having decreased fish odor of the present invention produces little fish odor which has bad organoleptic influences. Further, since the fish oil having decreased fish odor of the present invention contains a high amount of highly unsaturated fatty acids such as DHA and EPA, the fish oil is suitable for use as food materials and it may be used also as materials for medical supplies.

While the present invention has been described in detail and with reference to specific examples thereof, it will be apparent to one skilled in the art that various changes and modifications can be made therein without departing from the spirit and scope thereof.

What is claimed is:

1. A method for preparing fish oil having decreased fish odor, which consists essentially of slightly hydrogenating fish oil selected from the group consisting of sardine oil, mackerel oil, tuna oil, skipjack oil, tuna orbital fat and skipjack orbital fat under the following non-selective conditions:

(1) an amount of catalyst used in the hydrogenation is 0.05% by weight or more to an amount of the fish oil;

(2) a hydrogen pressure in gaseous phase at the beginning of the hydrogenation is 3 $kg/cm^2$ or more;

(3) a reaction temperature of the hydrogenation is in the range of from 90° to 150° C.; and (4) a reaction time of the hydrogenation is in the range of from 5 to 30 minutes, so as to have a decrease rate of iodine value of 15% or less and a decrease rate of highly unsaturated fatty acid of 33% or less.

2. A method for preparing fish oil having decreased fish odor as in claim 1 wherein the catalyst is a nickel catalyst.

3. A method for preparing fish oil having decreased fish odor as in claim 1, wherein the highly unsaturated fatty acid is docosahexaenoic acid (DHA).

4. A method for preparing fish oil having decreased fish odor as in claim 1, wherein the highly unsaturated fatty acid is eicosapentaenoic acid (EPA).

5. Sardine oil having decreased fish odor prepared by the method of claim 1.

6. Sardine oil having decreased fish odor as in claim 5, having the following characteristics:

(1) a concentration of DHA contained in fatty acid residue of the oil is in the range of from 1 to 13% by weight;

(2) a concentration of EPA contained in fatty acid residue of the oil is in the range of from 3 to 18% by weight: and (3) a content of trans-isomer is 4% by weight or more.

7. Mackerel oil having decreased fish odor prepared by the method of claim 1.

8. Mackerel oil having decreased fish odor as in claim 7, having the following characteristics:

(1) a concentration of DHA contained in fatty acid residue of the oil is in the range of from 1 to 13% by weight;

(2) a concentration of EPA contained in fatty acid residue of the oil is in the range of from 3 to 18% by weight; and (3) a content of trans-isomer is 4% by weight or more.

9. Tuna oil having decreased fish odor prepared by the method of claim 1.

10. Tuna oil having decreased fish odor as in claim 9, having the following characteristics:

(1) a concentration of DHA contained in fatty acid residue of the oil is in the range of from 15 to 25% by weight;

(2) a concentration of EPA contained in fatty acid residue of the oil is in the range of from 1 to 10% by weight; and (3) a content of trans-isomer is 4% by weight or more.

11. Skipjack oil having decreased fish odor prepared by the method of claim 1.

12. Skipjack oil having decreased fish odor as in claim 11, having the following characteristics:

(1) a concentration of DHA contained in fatty acid residue of the oil is in the range of from 15 to 25% by weight;

(2) a concentration of EPA contained in fatty acid residue of the oil is in the range of from 1 to 10% by weight; and (3) a content of trans-isomer is 4% by weight or more.

13. Tuna orbital fat having decreased fish odor prepared by a method of claim 1.

14. Tuna orbital fat having decreased fish odor as in claim 13, having the following characteristics:

(1) a concentration of DHA contained in fatty acid residue of the oil is in the range of from 25 to 38% by weight;

(2) a concentration of EPA contained in fatty acid residue of the oil is in the range of from 2 to 8% by weight; and (3) a content of trans-isomer is 4% by weight or more.

15. Skipjack orbital fat having decreased fish odor prepared by a method of claim 1.

16. Skipjack orbital fat having decreased fish odor as in claim 15, having the following characteristics:

(1) a concentration of DHA contained in fatty acid residue of the oil is in the range of from 25 to 38% by weight;

(2) a concentration of EPA contained in fatty acid residue of the oil is in the range of from 2 to 8% by weight; and (3) a content of trans-isomer is 4% by weight or more.

17. A method for preparing fish oil having decreased fish odor, which consists essentially of:

slightly hydrogenating fish oil selected from the group consisting of sardine oil, mackerel oil, tuna oil, skipjack oil, tuna orbital fat and skipjack orbital fat under the conditions that:

(1) an amount of catalyst is used in the hydrogenation of 0.05% by weight or more to an amount of the fish oil, (2) hydrogen pressure in a gaseous phase at the beginning of the hydrogenation is 3 $kg/cm^2$ or more, (3) reaction temperature of the hydrogenation is in the range of from 90° to 150° C., and (4) the hydrogenation is carried out for a time between five to thirty minutes sufficient to hydrogenate the fish oil to have a decreased rate of iodine value of 15% or less, and a decreased rate of highly unsaturated fatty aliphatic acids of docosahexaneoic acid and eicosapentaenoic acid of 33% or less.

* * * * *